United States Patent [19]

Edwall et al.

[11] 4,119,498

[45] Oct. 10, 1978

[54] MONOCRYSTALLINE METAL ELECTRODE AND METHOD OF USE

[76] Inventors: Nils Erik Gunnar Edwall, Storskiftesvägen, S-145 60 Norsborg; Göran Sven Eklund, Karl Martins väg 17, S-185 00 Waxholm, both of Sweden

[21] Appl. No.: 815,061

[22] Filed: Jul. 12, 1977

[30] Foreign Application Priority Data

Jul. 13, 1976 [SE] Sweden .............................. 7607993

[51] Int. Cl.$^2$ ...................... G01N 27/30; G01N 27/56
[52] U.S. Cl. ...................................... 204/1 T; 128/2 E; 204/195 R; 204/195 P; 204/195 F; 204/195 B; 324/30 R

[58] Field of Search ............... 204/292, 195 R, 195 P, 204/195 F, 195 B, 1 T, 1 Y, 1 P, 1 K, 1 H, 1 N; 128/2 E, 2.1 E; 324/30 R, 29

[56] References Cited

U.S. PATENT DOCUMENTS 3,298,944  1/1967  Luck ............................... 204/292 X Primary Examiner—G. L. Kaplan
Attorney, Agent, or Firm—Burns, Doane, Swecker & Mathis

[57] ABSTRACT

An improved metal electrode for the determination of pH, $P_{O_2}$ or $P_{CO_2}$ in liquids is disclosed. The improved electrode consists of a metal sensor (e.g., antimony) in a holder characterized in that the metal is monocrystalline with only one plane crystal face exposed to the liquid.

5 Claims, 14 Drawing Figures

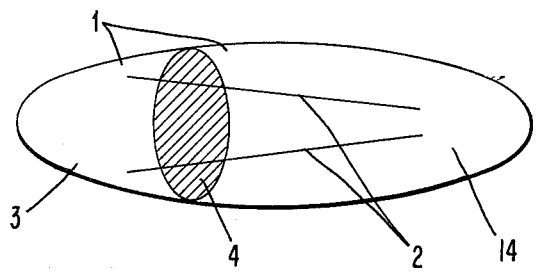
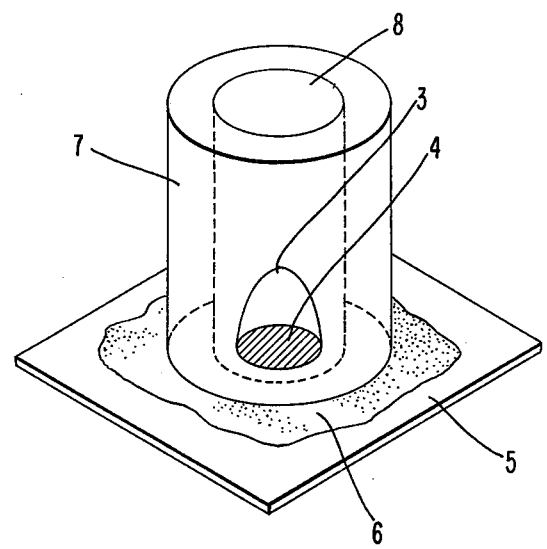
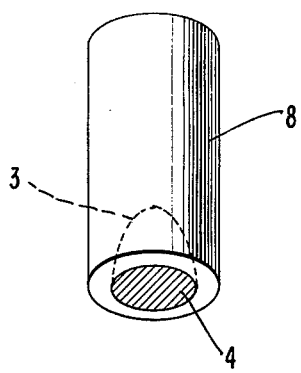
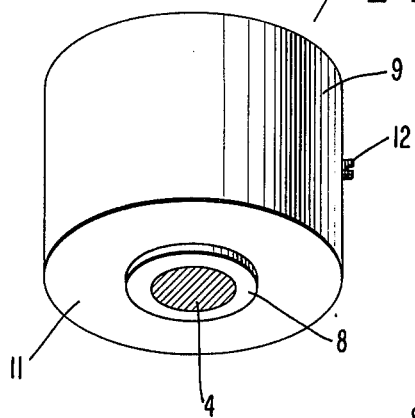
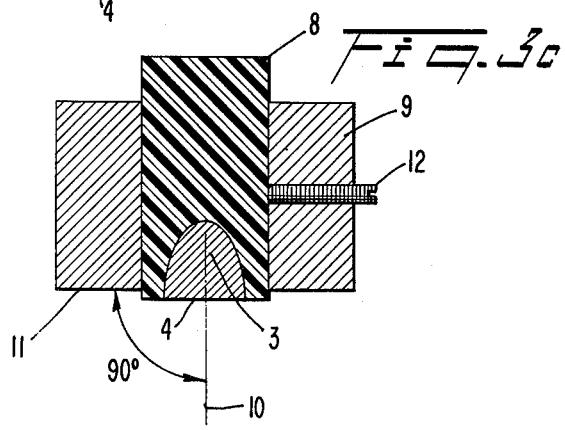
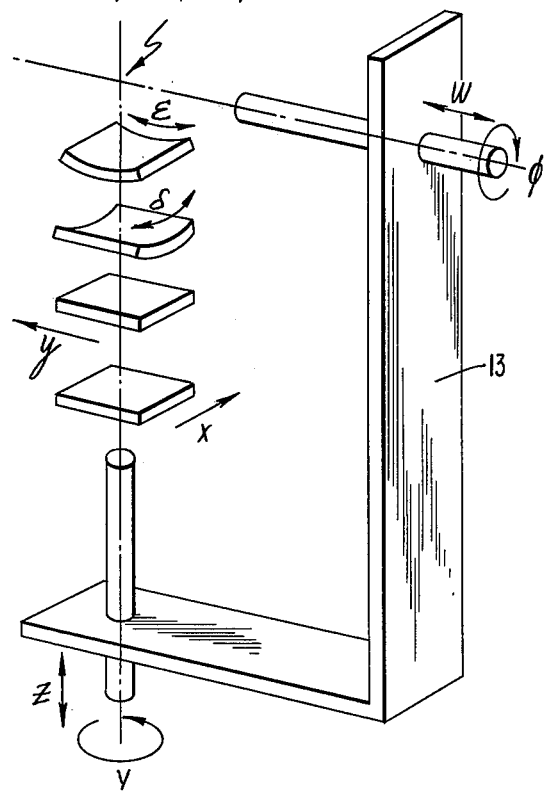

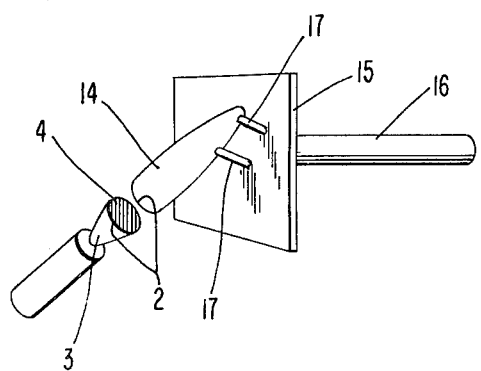
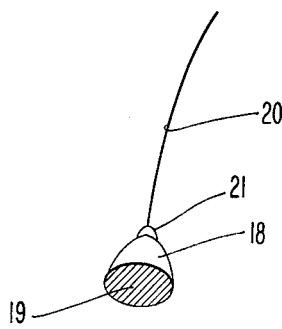
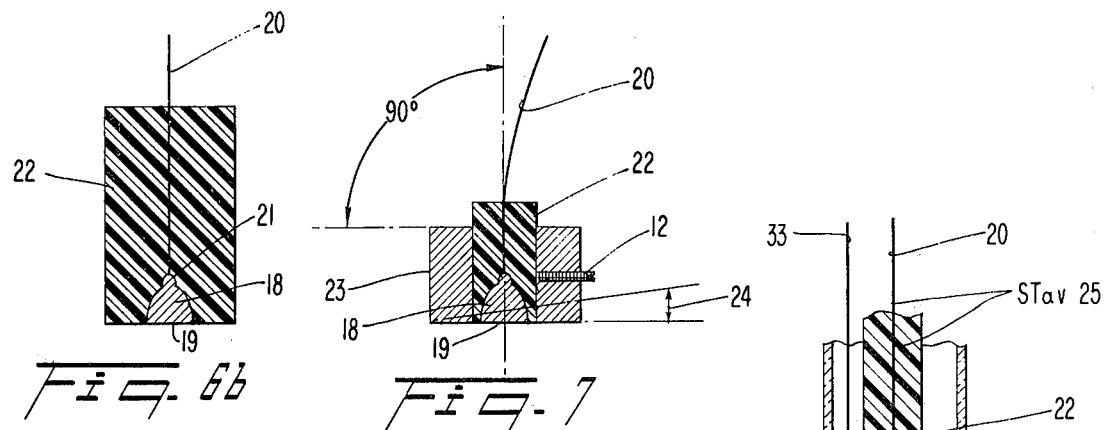
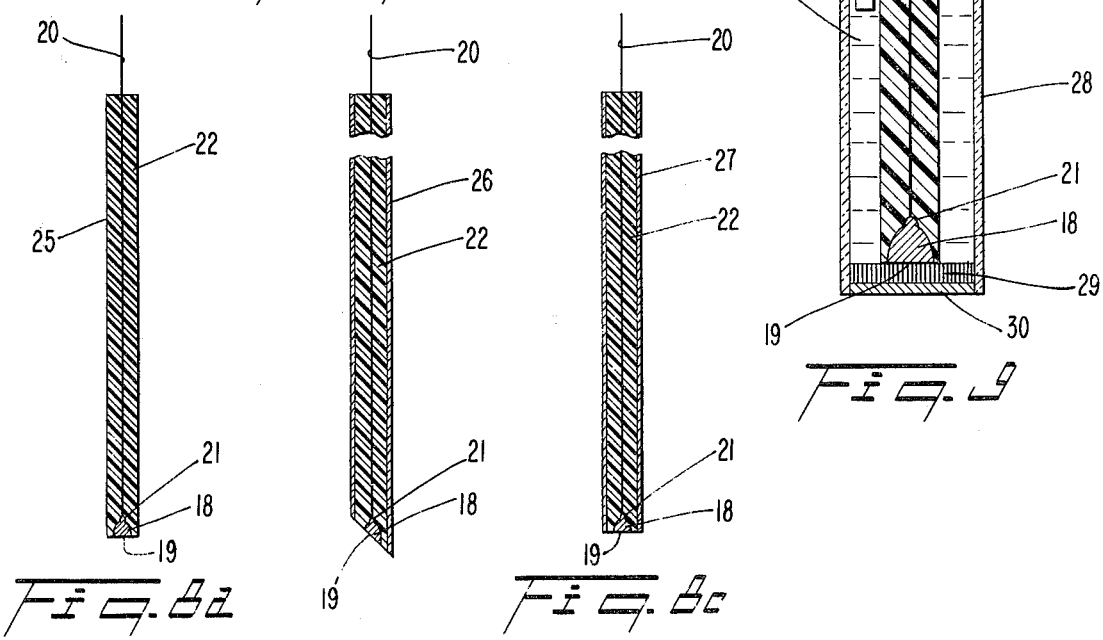

MONOCRYSTALLINE METAL ELECTRODE AND METHOD OF USE

BACKGROUND OF THE INVENTION

The present invention concerns an electrode for the measurement of liquids. The electrode which has a metal sensing element contained in a holder, is intended primarily for the determination of pH, but can also be used for the measuring of $P_{O_2}$ and $P_{CO_2}$.

The measurement of pH and other quantities in liquids is very important in many connections. Such measurements are carried out in a routine fashion in many laboratories and in technical operations. Measuring electrodes of this type have also been developed for medicinal applications.

The best known and most widely used pH electrodes have been glass electrodes. The latter must be made with very thin glass walls and are therefore very sensitive to mechanical stress. This makes necessary special handling and safekeeping, which limit their exploitation. The glass electrode, moreover, cannot be produced with the small, precise dimensions necessary for many uses if the required measuring precision is to be maintained.

Metal electrodes have greater mechanical stability. Such electrodes with sensors of iridium, palladium, antimony, and platinum have been developed for various purposes, e.g., for the measuring of pH in soil. Another example would be miniaturized electrodes for the in vivo measuring of pH in blood. These electrodes, however, have proved to have poor stability and are difficult to reproduce, and the variations between different electrodes are considerable. They are, moreover, at least in certain cases, sensitive to impurities from other metal ions in the testing liquid, and they can also show sensitivity to touch of the electrode surface and to agitation of the testing liquid. The known technique is described, for example, in U.S. Pat. No. 2,416,949, German Patent Application 2,333,641, and Swedish Pat. Nos. 384,921 and 384,922.

The purpose of the present invention, therefore, is to provide a metal electrode which is suited for miniaturization. It is also to provide an electrode which possesses stability and is reproducible over long and short periods. The electrode is also intended to withstand normal handling and to be minimally sensitive to variations in normally occurring impurities in the testing liquid.

It has proved possible to attain these qualities and other advantages, as, for example, reproductiveness between individual electrodes, by means of metal electrodes according to the present invention which are characterized in that the metal sensor is a monocrystalline metal with only one plane crystal face exposed to the liquid being tested for pH, $P_{O_2}$ or $P_{CO_2}$. Electrodes according to the present invention make possible exact long-period and short-period measurements of pH in smaller testing amounts than has been the case hitherto with known polycrystalline metal electrodes. Electrodes according to the invention, moreover, require considerably less calibration than is necessary with glass electrodes. A particular embodiment of the present invention is constituted by the use of "whiskers", which are single crystals with only one dislocation.

DESCRIPTION OF THE DRAWINGS

The invention is illustrated below by means of an example in connection with the following figures:

FIG. 1 shows the starting material for the production of the electrodes;

FIG. 2 shows the material embedded for further treatment;

FIGS. 3a, 3b, and 3c show the assembling of the material for grinding;

FIG. 4 shows the principle for the goniometer which is used in X-ray diffraction equipment for determination of the crystal plane;

FIG. 5 shows a test holder for the orientated material;

FIGS. 6a, 6b and 7 show successive stages in the assembling and grinding process for the electrodes;

FIGS. 8a, 8b, and 8c show different types of electrodes according to the invention; and FIG. 9 shows another type of electrode according to the present invention.

DETAILED DESCRIPTION OF THE INVENTION

The method explained below concerns electrodes of antimony, but in principle it may also be used for electrodes of other metals.

The starting material, 99.95% of pure antimony in pieces, is melted and additionally purified by means of repeated zone refining under protective or inert gas. From the material refined in this way there is produced a large single crystal with utilization of the Bridgeman technique (Proc. Am. Acad. Sci., 60, 305 - 1925). The orientation of the crystallographic main axes in the single crystal obtained is generally unknown or only approximately known. The following method has therefore been applied in order to produce electrodes with a known exposed crystal face as the measuring face.

The large single crystal 1 (FIG. 1) is provided with longitudinal lines 2 at different places along its periphery, whereupon a smaller part of the crystal is separated by means of spark cutting with a continuous wire. This piece 3 is then cast into epoxy (FIG. 2).

The metal piece 3 is placed with its, spark-cut face 4 turned down on a disk of plexiglas 5, previously provided with a thin layer of silicon grease 6 or some other release agent. A polytetrafluoroethylene ring 7 is placed above the disk 5, enclosing the metal piece. Into the mold formed in this way is poured a hardening epoxy resin.

When the epoxy has hardened, the epoxy pellet 8 is discharged with the embedded antimony piece 3 (FIG. 3) from the mold and is placed in a ring-shaped, well-fitting grinding holder of stainless steel 9, constructed in such a way that the epoxy pellet's longitudinal axis 10 is at right angles to the under side 11 of the holder. The fixing of the epoxy pellet 8 to the holder 9 is effected by means of a locking screw 12, so that only a very small part of the end of the pellet in which the antimony piece 3 is embedded is under the holder's lower side 11. The antimony face 4 is ground according to normal crystallographic procedure by carefully grinding the epoxy pellet on wet carborundum abrasive paper (400 and 600 mesh respectively) and followed by a polish with 1 μm diamond paste. This process yields a very bright, crystallographically undisturbed metal face which continues to be parallel with the original sectional area 4.

The metal piece 3 is again freed from the epoxy by the dissolution of the same in trichloroethylene, and it is installed in an X-ray diffraction goniometer 13. This goniometer has four linear degrees of freedom ($x, y, z,$ and $w$ in FIG. 4) and four rotation degrees of freedom ($\phi, \ominus, \delta,$ and $\epsilon$ in FIG. 4).

The goniometer 13 is installed in an X-ray diffraction apparatus provided with a goniometer of the Bragg spectrometer type, described in detail by Guinier (X-ray Chrystallographic Technology, London, 1952), with the axis $w$ (FIG. 4) coinciding with the axis of the "Bragg goniometer". Through adjustment of $x, y, z$ (FIG. 4) the antimony face 4 is brought into position for the reception of X-ray reflections from it, whereby the $y$ and $w$ axes coincide at the beginning of the orientation. The "Bragg goniometer" is installed for the reception of reflections from a definite crystal plane (e.g., the trigonal $(11\bar{1})$ plane), and with small adjustments of $\epsilon$ the goniometer 13 is rotated through the angle $\phi$ until the reflection is obtained. The goniometer 13 is re-orientated while the reflection continues to be obtained, by the adjustment of $\delta$, so that a perpendicular to its $x$-$y$ plane forms a bisector to the angle between the primary X-ray and the diffracted X-ray (whereby the crystal plane chosen comes to be orientated perpendicularly to the $z$ axis). The "Bragg goniometer" is adjusted for the reception of reflections from another crystal plane (e.g., the trigonal (001) plane, and with small adjustments of $\gamma$ (i.e., rotation around the $z$ axis) goniometer 13 is again rotated through $\phi$ until the reflection is obtained. When this is the case, the goniometer's $w$ axis coincides with the dividing line between the two crystallographic planes chosen (i.e., with the trigonal $[1\bar{1}0]$ direction in the example selected here). By studying the relative position of the last determined plane (whose perpendicular is a bisector to the primary ray and the diffracted ray) and of the previously determined plane (which is perpendicular to the $z$ axis) it can be determined whether the crystallographic direction which constitutes the plane's intersection or dividing line ( $[1\bar{1}0]$ the direction in the example chosen) is parallel or anti-parallel with the $w$ axis. With this as the starting point, the position of the crystallographic main axes in the antimony piece 3 can be fixed. This information is transferred thus to the greater part 14 of the original single crystal 1.

The larger part of the single crystal 14 is installed on a micro-manipulator and is carefully joined to the orientated part 3 (which continues to be installed in goniometer 13) by adjusting the manipulator. A good fitting is assured by the earlier drawn lines 2. Piece 14 is attached to a fixture so orientated that it contains the crystallographic information. In FIG. 5, for example, a metal plate 15 can be set up perpendicular to the $w$ axis 16 of the goniometer 13 not shown), and the piece 14 is fixed to this plate by means of metal wire supports 17 and epoxy adhesive. On this metal plate (which defines the trigonal $(1\bar{1}0)$ plane) the projection of the $(\bar{1}\bar{1}1)$ plane is further marked. This information (together with the knowledge of which side of plate 15 has the $[1\bar{1}0]$ direction to normal) contains all the data necessary for determining the position of the crystallographic main axes in the larger part 14 of the single crystal 1 as well.

When the position of the crystal axes in the single crystal 14 is known, as indicated above, then the latter is cut parallel with a known crystal plane or perpendicular to a known crystal direction. The cutting is carried out by means of spark cutting with continuous wire. By means of repeated spark cutting it is possible to produce metal pieces 18 of the shape and size considered desirable, having a plane limitation surface 19 parallel with a crystallographic plane of known (or chosen) symmetry. The parts 18 produced in this manner are degreased in trichlorethylene. On the metal piece 18 there is attached, preferably on the reverse side of face 19, a lacquer-insulated copper wire 20 of suitable dimensions with conductive silver epoxy 21 (FIG. 6). All faces except the boundary face 19 are insulated, for example, by embedding the piece 18 in plastic (e.g., epoxy) 22 in the manner corresponding to the one described above in the case of the small single crystal piece 3 (FIG. 6). The boundary surface 19 is ground and polished gently with wet abrasive paper and diamond paste, as described above in connection with piece 3.

The agreement with the desired crystallographic plane, of boundary surface 19 is controlled with X-ray diffraction according to the method described by Guinier. In case a deviation is observed, it is corrected by renewed grinding and polishing in the correct direction. In this connection a grinding holder 23 of stainless steel can be employed with suitable angle correction 24 (FIG. 7).

If the electrode is to function well, the electrode surface must be plane and continuous. Cracks and flaws in which other crystallographic planes than the intended one are exposed must not occur either in face 19 or in its boundary toward epoxy 22. Very small cracks into which no liquid can penetrate may be tolerated under certain circumstances. The qualities of the electrodes suffer somewhat because of these very small cracks but they are still considerably better than previously known electrodes.

According to the process, the electrodes may be produced in the form desired. They may, for example, be given the form of rod electrodes 25, of electrodes placed in cannulae 26 or in catheters 27 (FIG. 8).

The electrodes described constitute an electro-chemical half cell which can be connected with the conductor 20 to an electrometer. The other half cell necessary for the measuring can consist of a conventional calomel or silver/silver chloride reference electrode, connected to the same measuring instrument, which electrode is in contact with the measuring solution into which the face 19 of the electrodes described is lowered.

A metal electrode as described above in some of its embodiments, i.e., a rod electrode 25, may also be used for determination of $P_{O_2}$ or $P_{CO_2}$ in a liquid phase.

A design of such an electrode is illustrated in FIG. 9. A rod electrode 25 is placed into a gas impermeable cylindrical tube 28 so that the surface 19 of the electrode is in contact with a porous, chemically inert spacer 29, which separates the surface 19 from a chemically inert membrane 30 which is permeable to gases but not to liquids. The membrane 30 is also a seal of the cylindrical tube 28. The space between the tube 28 and the rod electrode 25, and also the pores of the spacer 29, are filled with an inner reference solution 31 into which also a reference electrode 32, e.g., a silver/silver chloride electrode, is immersed. In a $P_{CO_2}$-application, the reference solution can be a bicarbonate- and chloride-ion containing solution while in a $P_{O_2}$-application it can be a buffer solution, e.g., TRIS, to which chloride ions have been added.

The electrode is immersed into the test solution, whereby the gas diffuses through the membrane 30 and equilibrates with reference solution 31. In the $P_{CO_2}$-electrode this changes the pH of the reference solution 31, which is recorded as a change of potential between conductors 20 and 33. For the $P_{O_2}$-electrode, changes in $P_{O_2}$ in the reference solution 31 cause a recordable variation of the potential between conductors 20 and 33 due to the sensitivity of the metal electrode to the oxygen partial pressure. By using a buffer as reference solution 31 electrode potential changes due to pH changes are avoided.

The principles, preferred embodiments and modes of operation of the present invention have been described in the foregoing specification. The invention which is intended to be protected herein, however, is not to be construed as limited to the particular forms disclosed, since these are to be regarded as illustrative rather than restrictive. Variations and changes may be made by those skilled in the art without departing from the spirit of the invention.

What is claimed:

1. An electrode for the measurement of pH, $P_{O_2}$ or $P_{CO_2}$ in liquids, including a metal sensor in an insulating holder said metal sensor having a surface adapted to contact said liquids characterized in that the said metal is monocrystalline manufactured and arranged to provide only one plane crystal face for exposure to the said liquid.

2. An electrode according to claim 1 wherein the metal is antimony.

3. An electrode according to claim 1 in the form of a rod.

4. In a method for the measurement of pH, $P_{O_2}$ or $P_{CO_2}$ in a liquid wherein an electrode is exposed to the liquid, the improvement comprising using as the electrode the electrode of claim 1.

5. In the method of claim 4 wherein the metal is antimony.

* * * * *